(12) United States Patent
Simonton et al.

(10) Patent No.: US 7,905,884 B2
(45) Date of Patent: Mar. 15, 2011

(54) METHOD FOR USE OF DILATING STYLET AND CANNULA

(75) Inventors: T. Andrew Simonton, Memphis, TN (US); Jeff J. Justis, Germantown, TN (US); Keith Matthew Kinnane, Bartlett, TN (US); Sean M. Haddock, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1019 days.

(21) Appl. No.: 11/412,341

(22) Filed: Apr. 27, 2006

(65) Prior Publication Data

US 2007/0255281 A1 Nov. 1, 2007

(51) Int. Cl.
*A61B 17/00* (2006.01)
*A61M 5/00* (2006.01)
(52) U.S. Cl. .................. 606/79; 606/86 R; 604/164.01; 604/165.01; 604/165.02
(58) Field of Classification Search .................. 600/567; 606/79, 86 R; 604/164.01, 165.01–165.02
See application file for complete search history.

(56) References Cited

U.S. PATENT DOCUMENTS

| | | | |
|---|---|---|---|
| 3,994,287 A | 11/1976 | Turp et al. | |
| 4,793,363 A | 12/1988 | Ausherman et al. | |
| 4,838,282 A | 6/1989 | Strasser et al. | |
| 5,257,632 A | 11/1993 | Turkel et al. | |
| 5,263,937 A | 11/1993 | Shipp | |
| 5,295,974 A | 3/1994 | O'Laughlin | |
| 5,385,151 A | 1/1995 | Scarfone et al. | |
| 5,772,661 A | 6/1998 | Michelson | |
| 5,868,684 A | 2/1999 | Akerfeldt et al. | |
| 5,957,832 A | 9/1999 | Taylor et al. | |
| 6,019,776 A * | 2/2000 | Preissman et al. | ............ 600/567 |
| 6,080,155 A | 6/2000 | Michelson | |
| 6,224,607 B1 | 5/2001 | Michelson | |
| 6,264,618 B1* | 7/2001 | Landi et al. | .................... 600/567 |
| 6,325,812 B1 | 12/2001 | Dubrul et al. | |
| 6,554,778 B1 | 4/2003 | Fleming, III | |
| 6,582,439 B1 | 6/2003 | Sproul | |
| 6,638,253 B2 | 10/2003 | Breznock | |
| 6,641,564 B1 | 11/2003 | Kraus | |
| 6,890,308 B2 | 5/2005 | Islam | |
| 2002/0177897 A1 | 11/2002 | Michelson | |
| 2003/0191414 A1* | 10/2003 | Reiley et al. | .................... 600/567 |
| 2003/0236506 A1 | 12/2003 | Schofield et al. | |
| 2007/0255282 A1 | 11/2007 | Simonton et al. | |

FOREIGN PATENT DOCUMENTS

| | | |
|---|---|---|
| DE | 29 06 054 | 6/1980 |
| DE | 90 07 115 | 8/1990 |
| DE | 10 2004 024188 | 2/2006 |

* cited by examiner

*Primary Examiner* — Eduardo C Robert
*Assistant Examiner* — Julianna N Harvey
(74) *Attorney, Agent, or Firm* — Martin & Ferraro, LLP

(57) ABSTRACT

In one preferred aspect, a method is provided for inserting an instrument set having a tapered configuration into a patient. In another preferred aspect, a method is provided for inserting a cannula having an external threaded portion into bone. In yet another preferred aspect, a method is provided for forming and enlarging an opening in bone.

14 Claims, 4 Drawing Sheets

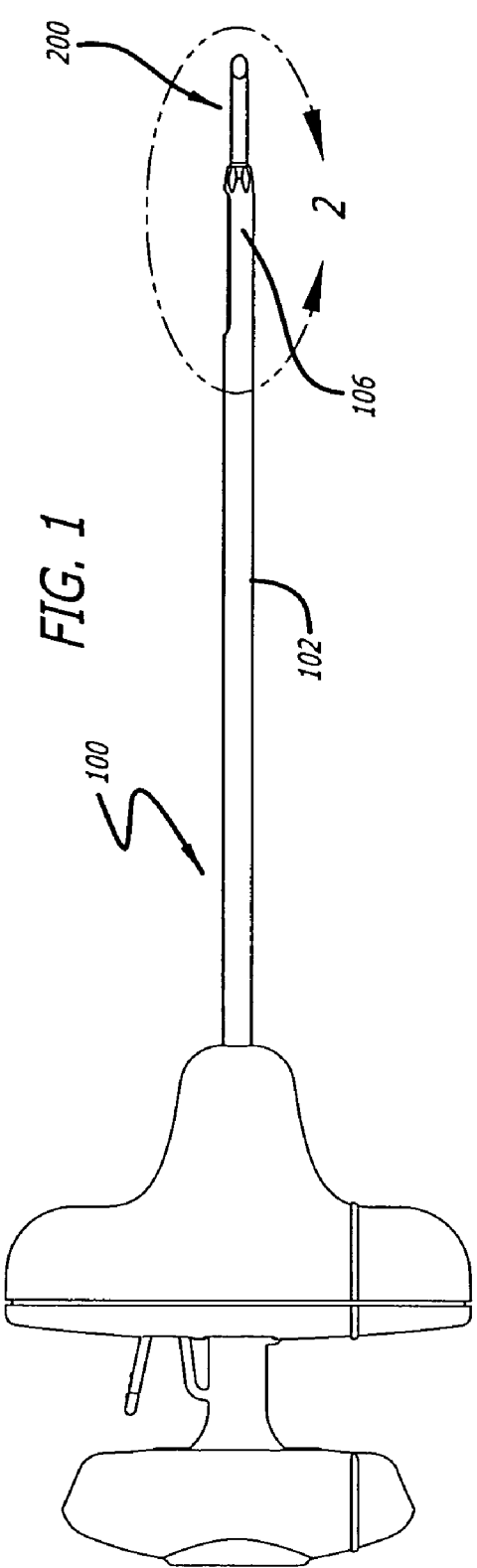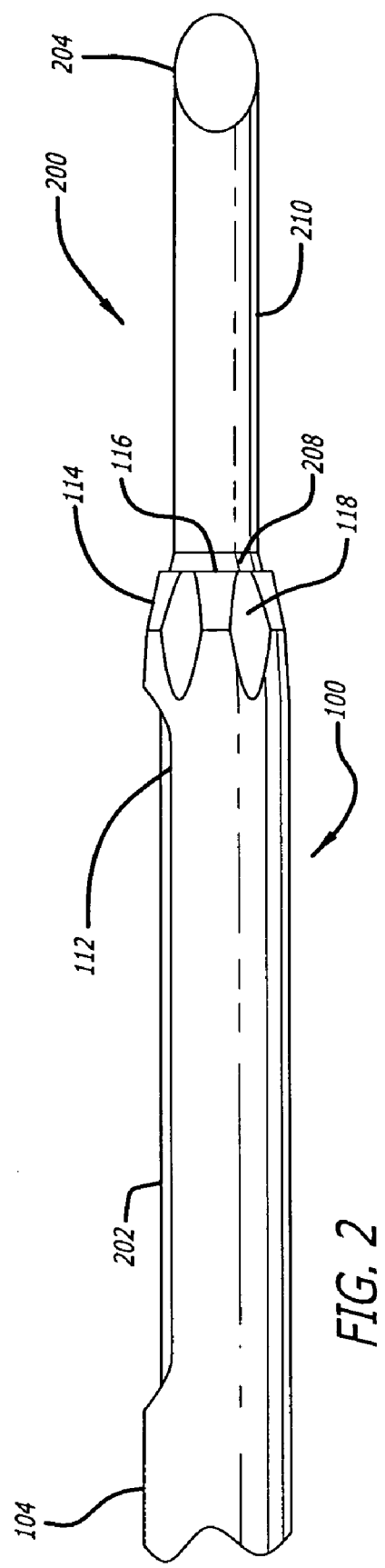

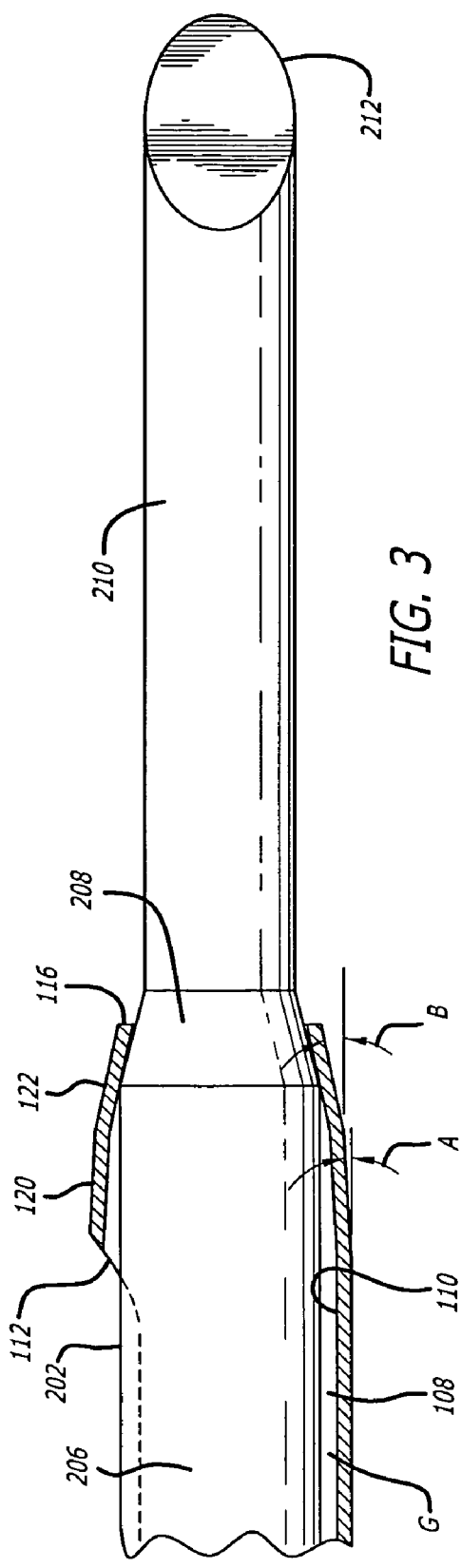
FIG. 3
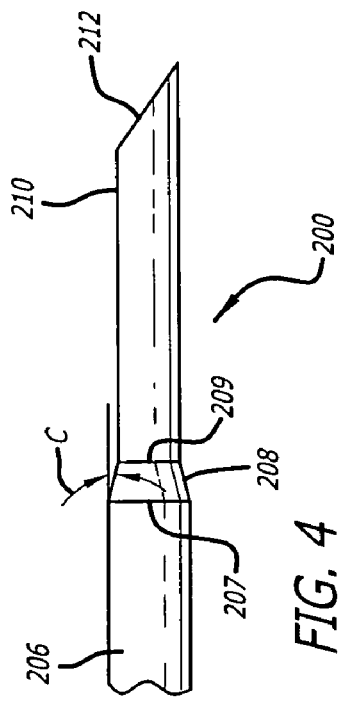
FIG. 4
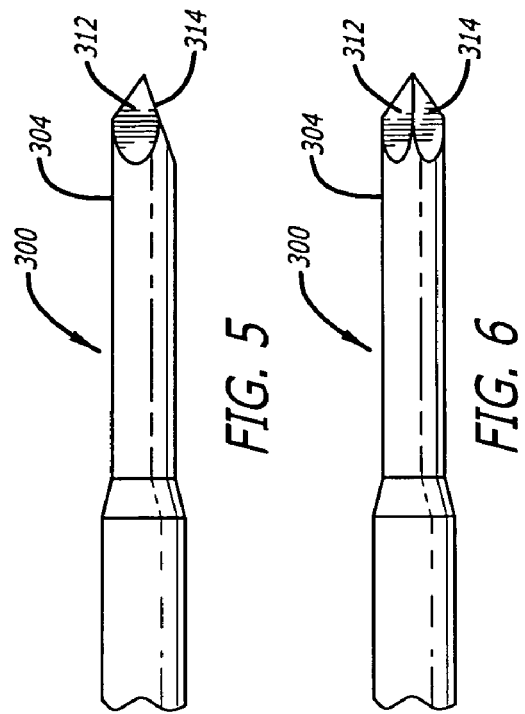
FIG. 5
FIG. 6

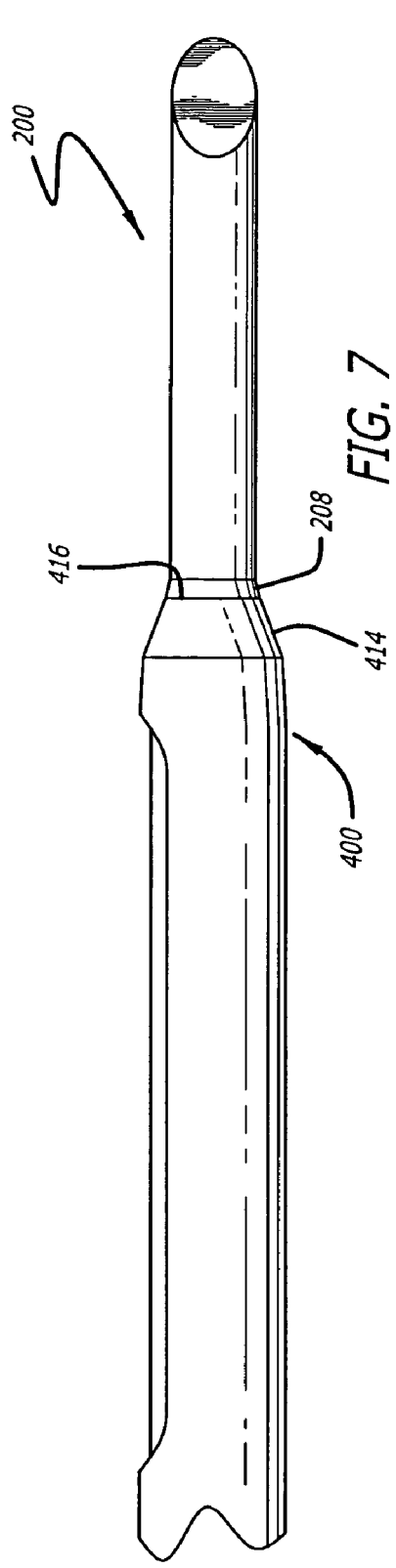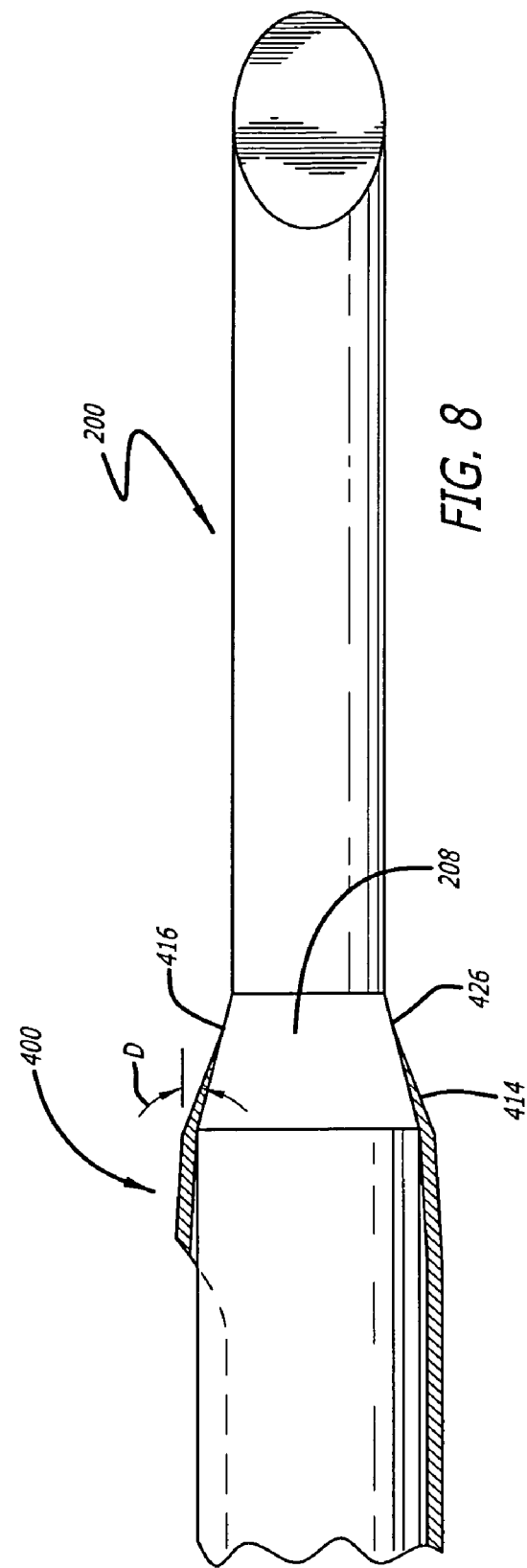

METHOD FOR USE OF DILATING STYLET AND CANNULA

BACKGROUND OF THE INVENTION

1. Field of the Invention

The present invention relates generally to a set of instruments having a distal tapered configuration for facilitating insertion of the instruments into a human body.

2. Description of the Related Art

Cannulas are used in surgical procedures to access tissue of the human body. To assist in the insertion of the cannula into the tissue, an instrument such as a stylet is inserted into the cannula to function as a guide for the cannula. Typically, the stylet has a diameter less than the diameter of the cannula, creating a stepped transition between the cannula distal end and the stylet. One problem encountered when using a conventional cannula and stylet is that the stepped transition between the cannula and stylet impairs the insertion of the instruments into the surrounding tissue because of the increased resistance encountered upon moving the stepped transition against the surrounding tissue. Therefore, there exists a need for an instrument set having a reduced surface profile in the transition between the distal end of the cannula and the inner instrument when the inner instrument extends from the distal end of the cannula so as to facilitate insertion of the instrument set into a patient and minimize disruption to the tissue of the patient.

Another problem associated with conventional cannulated instrument sets is that the distal end of a stylet when inserted together with the cannula protrudes a distance from the distal end of the cannula that is insufficient to optimally guide the instrument set into the surgical site of a patient, or optimally penetrate the tissue. Therefore there exists a need for an instrument set that when used with a stylet, will provide the surgeon with increased guidance for inserting the instrument set into the surgical site of the patient while reducing the effort needed for the instrument set to penetrate the tissue.

SUMMARY OF THE INVENTION

The present invention in one preferred embodiment includes a method for forming an opening in bone. The method includes providing a cannula having a distal end, a proximal end, a passage therethrough, and a mid-longitudinal axis, the distal end having an outer perimeter converging at an angle toward the mid-longitudinal axis of the cannula. The method further includes providing a stylet having a distal end, a proximal end, and a tapered transition portion proximate the distal end, the tapered transition portion having an angle approximating the converging angle of the outer perimeter of the distal end of the cannula, the stylet being sized and configured to be inserted into the passage of the cannula; placing the stylet into the cannula with at least a portion of the tapered transition portion and the distal end of the stylet extending beyond the distal end of the cannula, the cannula and the stylet forming a smooth transition between the angled portion of the stylet and the converging part of the cannula to facilitate introduction into bone; inserting the distal end of stylet into the bone; advancing into the bone the stylet and cannula together with the tapered transition portion of the stylet contacting the bone prior to the converging part of the cannula to form an opening into the bone, the opening having a reduced transverse dimension proximate the stylet and a larger transverse dimension proximate the cannula; and removing the stylet from the cannula with the cannula remaining in the bone.

In another preferred embodiment, the present invention includes a method for forming an opening into bone. The method includes providing a cannula having a distal end, a proximal end, a length therebetween, a passage along the length, and an exterior surface, the exterior surface including a thread along at least a portion of the length of the cannula; inserting the cannula through the bone by linear insertion with the bone sliding over the thread with the thread not engaging the bone to a depth in the bone proximate to a final insertion depth; further advancing the cannula into the bone by rotating the cannula to engage the thread of the cannula to the bone until the cannula is at the final depth of insertion, the cannula being in fixed relationship to the bone.

In a further preferred embodiment, the present invention includes a method for forming an opening in bone. The method includes inserting a stylet into a cannula, the cannula having a distal end, a proximal end, a passage therethrough, and a mid-longitudinal axis, the stylet having a distal end that extends beyond the distal end of the cannula when inserted therein; advancing into the bone the cannula and stylet in fixed relationship to each other along an axis of insertion to a first insertion depth at least in part into the bone to form an opening at a final insertion depth in the bone, the opening having a portion occupied by the stylet with a smaller transverse dimension than a portion of the opening occupied by the cannula; withdrawing the stylet from the cannula with the cannula remaining in the bone; and advancing the cannula further into the opening from the first insertion depth to a second insertion depth along the axis of insertion to enlarge at least a portion of the opening formed by the stylet.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1 is a side elevation view of an instrument set having a cannula and stylet in accordance with one embodiment of the present invention.

FIG. 2 is an enlarged partial side elevation view of a distal end of the instrument set of FIG. 1 along line 2 of FIG. 1.

FIG. 3 is a partial cross-sectional side view of the distal end of the cannula of FIG. 1 with the stylet of FIG. 1.

FIG. 4 is a partial side elevation view of the distal end of the stylet of FIG. 1.

FIG. 5 is a partial side elevation view of the distal end of a stylet in accordance with another preferred embodiment of the present invention.

FIG. 6 is a partial side elevation view of the stylet of FIG. 5 rotated approximately 90 degrees.

FIG. 7 is a partial side elevation view of a distal end of an instrument set having a cannula and stylet in accordance with another preferred embodiment of the present invention.

FIG. 8 is a partial cross-sectional side view of the distal end of the cannula of FIG. 7 and stylet of FIG. 1.

DETAILED DESCRIPTION OF THE PREFERRED EMBODIMENT

Figure 9:
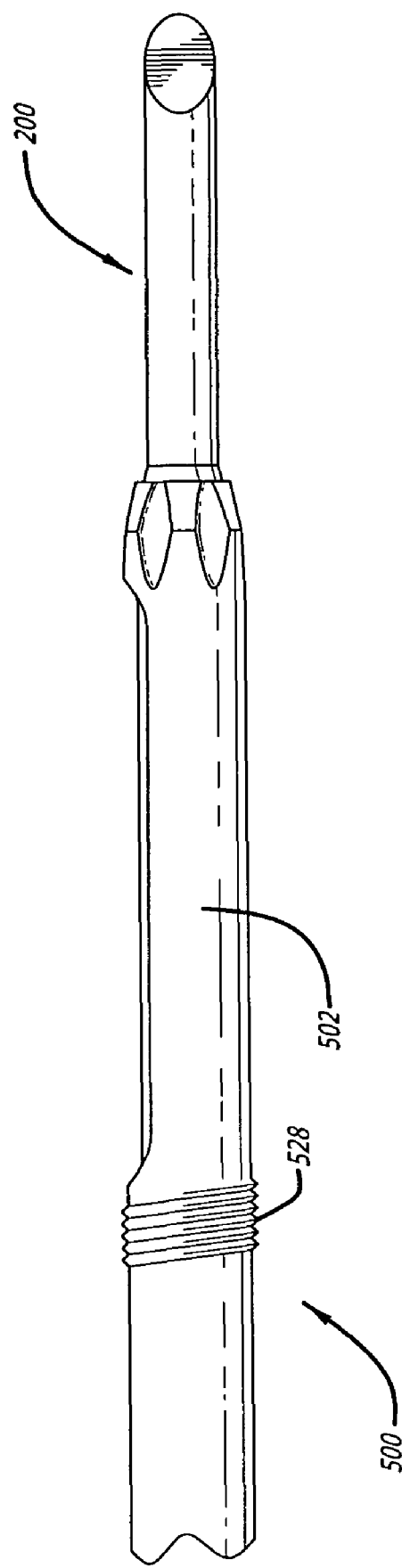
FIG. 9 is a partial side elevation view of a distal end of an instrument set having a cannula and stylet in accordance with another preferred embodiment of the present invention.

Reference will now be made in detail to the present preferred embodiments of the invention, examples of which are illustrated in the accompanying drawings.

FIGS. 1-3 illustrate an instrument set in accordance with one preferred embodiment of the present invention. Preferably, the instrument set includes a cannula and a stylet insertable at least in part into the cannula, the cannula and stylet each having a generally matching tapered profile adapted to facilitate insertion of the instrument set into the tissue of a patient, preferably into the bone of a patient. It will be appreciated by those of ordinary skill in the art that the tapered profile of the instruments set forth below may be adapted for use with other sets having two or more instruments.

As shown in FIGS. 1-3, cannula 100 is adapted to receive at least a portion of a stylet 200 therethrough. Cannula 100 includes a body 102, and exterior surface 104, a distal end 106, and a passage 108 having an interior surface 110. Cannula 100 also includes a window 112 proximate distal end 106. Window 112 is preferably sized and configured to permit the passage of a portion an instrument such as a bone displacement instrument therethrough.

Distal end 106 of cannula 100 includes an outer perimeter 114 having a distal edge 116 and may include a plurality of longitudinal serrations, grooves, or scallops 118. Serrations 118 cut into bone similar to a serrated knife. Serrations 118 preserve the strength of distal end 106 because they permit the wall of cannula 100 to retain a thickness sufficient to ensure that the distal end remains rigid while at the same time facilitates the insertion of cannula 100 into the surrounding tissue and bone. As shown in FIGS. 2 and 3, outer perimeter 114 is preferably tapered relative to the mid-longitudinal axis of cannula 100. The tapered portion of distal end 106 preferably includes two angled portions 120 and 122, but may include only one larger angled portion. The first angled portion 120 is preferably at an angle A relative to the mid-longitudinal axis of cannula 100. A preferred range for angle A is between 0 to 30 degrees relative to the mid-longitudinal axis of cannula 100. The second angled portion 122 is preferably at an angle B relative to the mid-longitudinal axis of cannula 100. A preferred range for angle B is between 0 to 30 degrees relative to the mid-longitudinal axis of cannula 100. Together, angled portions 120, 122 form a tapered profile generally in the range of 5 to 45 degrees, more preferably 10 to 45 degrees, and most preferably 15 degrees relative to the mid-longitudinal axis of cannula 100. It will be appreciated by those of ordinary skill in the art that outer perimeter 114 may have a single, continuous taper to distal edge 116, or more than two angled portions. It will be further appreciated that outer perimeter 114 may be curved in a plane parallel with the mid-longitudinal axis of the cannula so as to approximate the shape of a spherical or elongated dome.

As shown in FIGS. 2-4, stylet 200 includes a shaft 202 and a distal end 204. Shaft 202 includes a proximal portion 206, a transition portion 208, and a distal portion 210 having a bevel 212 at distal end 204. Portion 210 preferably has a reduced dimension to facilitate introduction into the tissue in a manner similar to that of a guide wire. As shown in FIG. 4, transition 208 is a tapered portion of shaft 202 that converges distally toward the mid-longitudinal axis of stylet 200 to provide a transition from a larger dimension of proximal portion 206 to a smaller dimension of distal portion 210 of shaft 202. The intersection of transition 208 and proximal portion 206 defines a proximal longitudinal limit 207 of transition 208. The intersection of transition 208 and distal portion 210 defines a distal longitudinal limit 209 of transition 208. Preferably, transition 208 is at an angle C relative to the mid-longitudinal axis of stylet 200. Angle C is preferably in the range of 5 to 45 degrees, more preferably 10 to 45 degrees, and most preferably 14 degrees relative to the mid-longitudinal axis of stylet 200.

As shown in FIG. 3, passage 108 of cannula 100 has a reduced portion proximate distal end 106 of cannula 100 that is sized and configured to have a transverse cross sectional dimension less than the transverse cross sectional dimension of proximal portion 206 of stylet 200. The reduced portion of passage 108 prevents stylet 200 from extending more than a predetermined distance beyond distal edge 116 of cannula 100 by preventing the larger dimension of proximal portion 206 of shaft 202 to pass therethrough. Preferably, angle C of transition 208 of stylet 200 is at an angle that is between angles A and B of cannula 100. It will be appreciated by those of ordinary skill in the art that the angles of distal end 106 of cannula 100 and of transition 208 of stylet 200 may be varied without departing from the scope of the present invention.

When assembled together, the angle of the over-all tapered profiled of outer perimeter 114 and the angle of transition 208 are each preferably within 15 degrees of each other, more preferably within 5 degrees of each other, and most preferably the same or approximately the same angle. Additionally, when fully assembled together, distal edge 116 of cannula 100 is adjacent transition 208 preferably between proximal and distal longitudinal limits 207, 209 of transition 208, both longitudinally and along the radial height of transition 208. Preferably, distal edge 116 is closer to distal longitudinal limit 209 of transition 208 more than proximal longitudinal limit 207 of transition 208. It will be appreciated that distal edge 116 may extend before or after the longitudinal limits of transition 208 when the cannula and stylet are assembled to present a smooth transition without departing from the scope of the present invention.

Referring to FIGS. 1-3, in a preferred method for inserting an instrument set such as described above into a human patient, a surgeon grasps the handle of stylet 200 (shown in FIG. 1) and places stylet 200 into cannula 100 with at least a portion of transition 208 and distal end 204 of stylet 200 extending beyond distal end 104 of cannula 100. If desired, the handles of the instruments may be configured to lock to one another. The surgeon then inserts distal end 204 of stylet 200 into the tissue such as the bone of the patient and continues advancing stylet 200, along with cannula 100, into the bone to form an opening into the bone. If desired, cannula 100 may be moved relative to stylet 200 and further advanced into the bone using stylet 200 as a guide wire. Stylet 200 may be withdrawn either partially or completely from cannula 100 with cannula 100 remaining in the bone. Cannula 100 may be further advanced into the bone after the withdrawal of stylet 200 if desired. The instrument set is preferably inserted to a depth sufficient to permit a surgeon to access bone through window 112. Once stylet 200 is withdrawn, the surgeon may insert other instruments through cannula 100, such as an instrument to displace bone through window 112. Cannula 100 may also be used to introduce a material therethrough. Examples of materials include a flowable material such as bone cement; other therapeutic materials such as bone morphogenetic protein, hydroxyapatite, hydroxyapatite tricalcium phosphate, or an anti-microbial substance; or a relatively solid and/or artificial material such as an implant.

The method is preferably performed in the spine of a human patient. It will be recognized that the instrument set and method of the present invention may be used in other areas of the human body.

Cannula 100 and stylet 200 are made of a surgical grade material. Examples of suitable materials include, but are not limited to, metal such as stainless steel and titanium, nitinol, carbon composites, and a plastic polymer. It will be appreciated that cannula 100 and stylet 200 may be made of any combination of metal, plastic, carbon composite, nitinol, or other material suitable for the intended purpose.

In a preferred embodiment of the present invention, cannula 100 has a maximum length along the mid-longitudinal axis of the cannula that is approximately 5.1 inches between the distal end and the handle. The thickness of the wall of the cannula is preferably approximately 0.015 inches. The maximum transverse dimension at distal end 106 of cannula 100 is preferably approximately 0.1 inches. The length of the tapered portion of distal end 106 is preferably generally 0.013 inches between the furthest distal extent of window 112 to distal edge 116. It will be appreciated that the dimensions set forth above may be varied without departing from the scope of the present invention.

Stylet 200 preferably has a length along the mid-longitudinal axis of approximately 6.1 inches between the handle and distal end 204. As shown in FIGS. 2 and 3, distal portion 210 of stylet 200 preferably has a length from the tip of distal end 204 to transition 208 that is greater than the length of transition 208, but less than the length of window 112 of cannula 100. In a preferred embodiment, distal portion 210 of stylet 200 has a length of approximately 0.5 inches. It will be appreciated that the dimensions set forth above may be varied without departing from the scope of the present invention.

Referring now to FIGS. 5 and 6, a stylet in accordance with another preferred embodiment of the present invention is shown and referred to by the reference number 300. Stylet 300 is similar to stylet 200 except that distal end 304 includes a plurality of facets 312, 314. It will be appreciated by those of ordinary skill in the art that the number and configuration of the facets may be varied without departing from the scope of the present invention. For example, as shown in FIG. 6, stylet 300 preferably includes a plurality of facets 312, 314 at an angle to each other. A third facet (not shown) extends on another side to form a tri-faceted configuration at distal end 304 of style 300.

Referring now to FIGS. 7 and 8, a cannula in accordance with another preferred embodiment of the present invention is shown and generally referred to by the reference number 400. As shown in FIG. 8, a cannula 400 is similar to cannula 100 except that distal edge 416 of cannula 400 forms a sharp edge. Additionally, outer perimeter 414 has an angled portion at an angle D which is preferably in the range of 10 to 45 degrees relative to the mid-longitudinal axis of cannula 400. Angle D has a steeper angle as compared to angle B shown in FIG. 3. The configuration shown in FIG. 8 permits a smoother transition 426 between distal edge 416 of cannula 400 and transition 208 of stylet 200. The nearly seamless transition 426 further facilitates insertion of the instrument set into the surrounding tissues of the patient at least in part due to the reduction of the surface profile of the leading end of the cannula.

Referring now to FIG. 9, a cannula in accordance with another preferred embodiment of the present invention is shown and generally referred to by the reference number 500. Cannula 500 is similar to cannula 100 except that body 502 includes a thread 528, proximate the distal end. Thread 528 is configured such that once the instrument set is partially inserted into the patient to a depth where thread 528 contacts bone, the surgeon may rotate cannula 500 about the mid-longitudinal axis and threadably secure cannula 500 to one or more bones of the patient. Thread 528 has a low profile thread height to allow cannula 500 to slide into tissue without significant engagement of the thread with the surrounding tissue. The furthest extent of thread 528 as measured along the mid-longitudinal axis of cannula 500 is preferably less than the maximum longitudinal extent of the tapered distal end portion of cannula 500. It will be appreciated that thread 528 may be configured and placed along the length of cannula 500 in a manner sufficient for the intended purpose of cannula 500. For example, as shown in FIG. 5, thread 528 is preferably configured to engage a pedicle of a vertebra of a human spine.

A preferred method for using the instrument set shown in FIG. 9 includes inserting by linear insertion the instrument set at least partially into the patient through a portion of bone and tissue; inserting the set to a depth until thread 528 contacts a portion of bone, such as a pedicle of a human spine; rotating cannula 500 about its mid-longitudinal axis to engage thread 528 within a portion of bone; and withdrawing stylet 200 from cannula 500. Once the procedure has been completed through cannula 500, cannula 500 is then rotated in the opposite direction of insertion to disengage cannula 500 from the bone of the patient.

The tapered configuration of the instrument set of the present invention is applicable to a wide variety of instruments. For example and without limitation, cannula 100 could be a sheath, sleeve, retractor, or any other tubular or cannulated member. Instrument 200 could be a stylet, obdurator, trocar, bone tamp, forceps, or any other instrument insertable in a tube having a portion adapted to extend beyond the distal end of the tube.

Advantages of the present invention include, for example, the ability of the user to more precisely place the instrument set within the patient. The tapered configuration of the present invention has the advantage of minimizing disruption of surrounding tissues and bone as the instrument set is being inserted into the patient. The tapered configuration of the cannula advantageously functions as a depth stop to the stylet to keep the distal end of the stylet from extending too far beyond the distal end of the cannula. An advantage of the longitudinal serrations at the distal end of the cannula is that the serrations facilitate insertion similar to a serrated knife to permit a more precise placement of the instrument set within the patient. An advantage of the thread shown in FIG. 9 is that the surgeon is able to attach the cannula to the patient to provide a more stable base for subsequent use of instruments through the cannula.

It will be appreciated by those of ordinary skill in the art that the present invention described above may take alternative forms without departing from the scope of the present invention. For example, distal portion 210 of shaft 202 of stylet 200 may be tapered along its length and may, if desired, have an angle substantially matching or precisely matching that of transition 208 to create an elongated taper. It will be appreciated that cannula 100 and stylet 200 need not have a circular cross section, but may have any other type of cross section suitable for the intended purpose. For example, the cross section of either instrument may be that of an elongated oval or other non-circular shape such as a square, or a shaft with a keel to prevent the inner instrument from rotating within the cannula.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for forming an opening in bone, the method comprising:
   providing a cannula having a distal end, a proximal end, a passage therethrough, and a mid-longitudinal axis, the distal end having an outer perimeter converging at an angle toward the mid-longitudinal axis of the cannula;

providing a stylet having a distal end, a proximal end, and a tapered transition portion proximate the distal end, the tapered transition portion having an angle approximating the converging angle of the outer perimeter of the distal end of the cannula, the stylet being sized and configured to be inserted into the passage of the cannula;

prior to insertion into the bone, placing the stylet into the cannula with at least a portion of the tapered transition portion and the distal end of the stylet extending beyond the distal end of the cannula, the cannula and the stylet forming a smooth transition between the angled portion of the stylet and the converging part of the cannula to facilitate introduction into bone;

inserting, with the stylet placed within the cannula, the distal end of stylet into the bone;

advancing simultaneously into the bone the stylet and cannula with the tapered transition portion of the stylet contacting the bone prior to the converging part of the cannula to form an opening into the bone, the opening having a reduced transverse dimension proximate the stylet and a larger transverse dimension proximate the cannula; and removing the stylet from the cannula with the cannula remaining in the bone.

2. The method of claim 1, further comprising providing the cannula having an exterior surface with threads, and threading the cannula into the bone to engage the cannula to the bone.

3. The method of claim 1, further comprising introducing an instrument through the cannula and into the bone.

4. The method of claim 1, further comprising introducing a material through the cannula into the bone.

5. The method of claim 4, wherein the material includes bone cement.

6. The method of claim 4, wherein the material includes a therapeutic material.

7. The method of claim 1, further comprising inserting a bone displacement instrument through the cannula and displacing bone proximate the distal end of the cannula.

8. The method of claim 1, wherein the providing the stylet further comprises providing the stylet with a non-tapered portion between the tapered transition portion and the distal end of the stylet.

9. A method for forming an opening in bone, the method comprising:

inserting a stylet into a cannula, the cannula having a distal end, a proximal end, a passage therethrough, and a mid-longitudinal axis, the stylet having a distal end that extends beyond the distal end of the cannula when inserted therein;

advancing simultaneously into the bone the cannula and stylet in fixed relationship to each other along an axis of insertion to a first insertion depth at least in part into the bone to form an opening at a final insertion depth in the bone, the opening having a portion occupied by the stylet with a smaller transverse dimension than a portion of the opening occupied by the cannula;

withdrawing the stylet from the cannula with the cannula remaining in the bone; and advancing, after the withdrawal of the stylet from the cannula, the cannula further into the opening from the first insertion depth to a second insertion depth along the axis of insertion to enlarge at least a portion of the opening formed by the stylet.

10. The method of claim 9, further comprising delivering a material through the cannula.

11. The method of claim 10, wherein the material includes bone cement.

12. The method of claim 10, wherein the material includes a therapeutic material.

13. The method of claim 9, further comprising inserting a bone displacement instrument through the cannula and displacing bone proximate the distal end of the cannula.

14. The method of claim 9, wherein inserting the stylet into the cannula includes inserting the stylet into the cannula until an enlarged portion of the stylet encounters a reduced portion of the passage of the cannula proximate the distal end of the cannula to block further insertion of the stylet through the cannula.

* * * * *